United States Patent [19]

Krueger

[11] Patent Number: 4,826,434

[45] Date of Patent: May 2, 1989

[54] DENTAL IMPLANT

[75] Inventor: Kenneth K. Krueger, Laguna Niguel, Calif.

[73] Assignee: Steri-Oss, Inc., Anaheim, Calif.

[21] Appl. No.: 921,351

[22] Filed: Oct. 20, 1986

[51] Int. Cl.$^4$ .............................................. A61C 8/00
[52] U.S. Cl. ................................................... 433/174
[58] Field of Search ............... 411/411, 413; 433/176, 433/175, 174, 173

[56] References Cited

U.S. PATENT DOCUMENTS

| | | | |
|---|---|---|---|
| 2,121,193 | 6/1938 | Hanicke | 411/413 |
| 2,472,103 | 7/1949 | Giesen | 433/174 |
| 4,010,545 | 3/1977 | Kilian et al. | 433/9 |
| 4,416,629 | 11/1983 | Mozsary et al. | 433/174 |
| 4,466,796 | 8/1984 | Sandhaus | 453/173 |
| 4,468,200 | 8/1984 | Munch | 433/174 |

*Primary Examiner*—Robert Peshock
*Attorney, Agent, or Firm*—Price, Gess & Ubell

[57] ABSTRACT

A desirable dental implant can be constructed out of titanium so as to have a first end for insertion into a jawbone, an externally threaded shank extending from said first end, a tapered head on said shank adjacent to the second end of the implant and an internally threaded bore shaped so as to include a non-round socket in the threads of said bore. The exterior of the implant is preferably etched so as to increase its area.

14 Claims, 1 Drawing Sheet

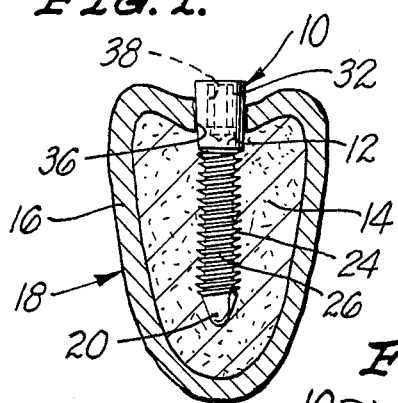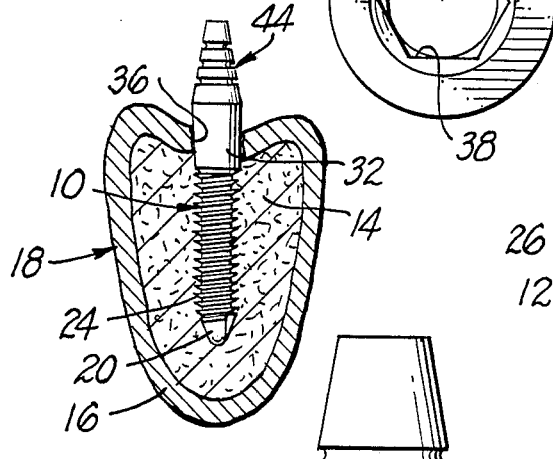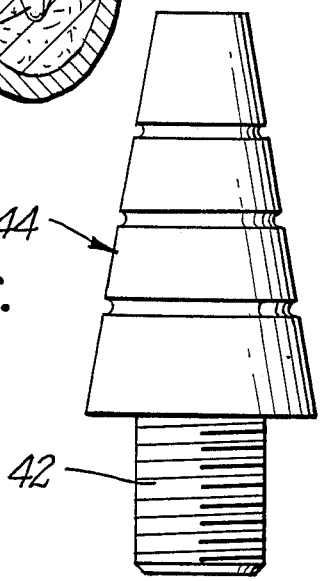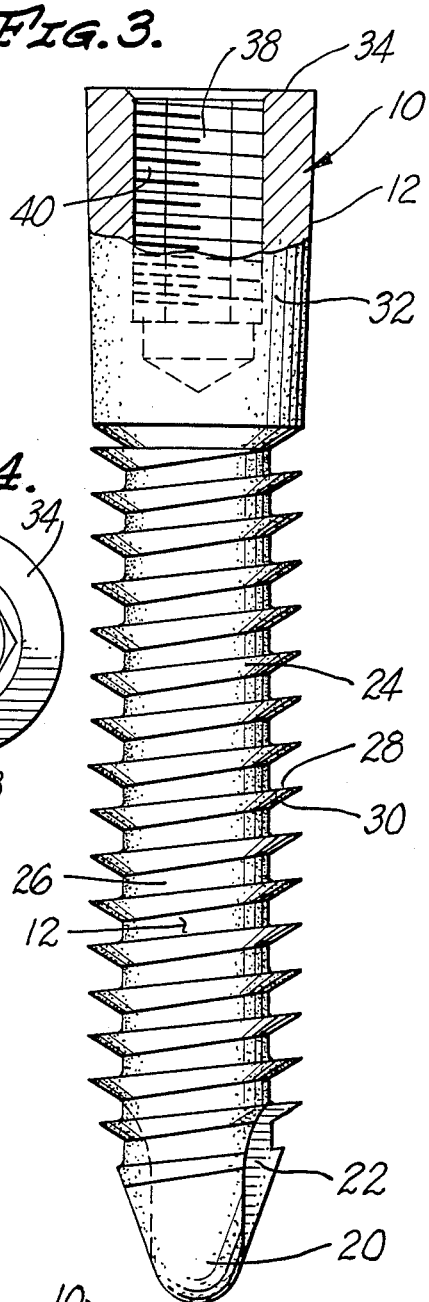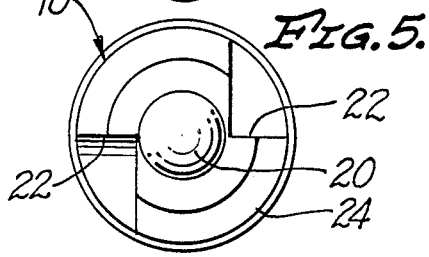

DENTAL IMPLANT

BACKGROUND OF THE INVENTION

The invention set forth in this specification pertains to new and improved dental implants.

The development of various biocompatible materials has resulted in a resurgence of interest in the development of dental implants. This in turn has led to the development of a wide variety of implant structures of various shapes and materials for use as replacements for natural teeth. An understanding of the present invention does not require a discussion of the various different structures which have been proposed and to some extent used as dental implants or of the various ways they have been used.

From a review of such prior implant structures it is possible to conclude that a number of factors have tended to restrict their widespread use. These include ease of insertion of an implant member, especially in those cases where the alveolar cavity to receive the implant does not precisely correspond to that of the implant. A related consideration concerns the need for an acceptable implant to fit with respect to the cortical portion of a jawbone so as to prevent soft tissue from invading the interior or medullary region of the jawbone as the implant remains in place after being installed in the jawbone.

The "holding" characteristics of an implant are also important to the acceptability of such a member. Critical questions relative to such characteristics are whether the shape of the implant will adequately engage the inner medullary portion within the outer or cortical portion of a jawbone to a sufficient extent that the implant will be held permanently in place. To be acceptable it also needs to be held in such a manner that the stresses and strains placed upon it during chewing are distributed in such a way as to minimize the chances of discomfort.

Another factor which is considered to have tended to restrict the use of prior implants relates to the mounting of a crown prosthesis upon them after they have been installed. In general the prior structures have normally been of such a character that there has been only one manner that a "tooth" or crown prosthesis could be mounted upon them. While this is frequently satisfactory, on occasion it is not desirable because of differing views as to the most desirable way of mounting a prosthesis.

BRIEF SUMMARY OF THE INVENTION

As a result of these and various related considerations it is believed that there is a need for new and improved dental implants. The broad purpose of the present invention is to provide implants which fulfill or meet such need.

From this it will be apparent that the invention is intended to provide implants: which may be easily and conveniently installed in the mouth; which when installed adequately seal the interior or medullary region of the jawbone against soft tissue invasion; which adequately "hold" in place in such a manner as to avoid or minimize possible discomfort; and which are of such a nature as to permit crown or "tooth" prostheses to be mounted upon them in different manners.

The invention is intended to provide all of such advantageous features within a single implant. However, it will be apparent that various aspects of a preferred implant of the invention can be used independently of other aspects or features of the invention in implant structures which are not as desirable as those utilizing all of the aspects or features of this invention. Because of this it is considered impossible to provide a precise summary of the invention which adequately indicates all aspects of the invention.

It is considered that advantages of this invention can be achieved by providing an elongated member serving as a dental implant, said member having a first end which is adapted to be located within the interior of an alveolar cavity and a second end which is adapted to be secured to a prosthetic crown, said member having a biocompatible exterior, in which the improvement comprises the use of at least one constructional feature from among those described in this document.

One of these features is the use of what may be termed a screw thread leading away from the first end of the member along the exterior of the member, the turns of this thread being spaced from one another so as to permit bone growth generally between these adjacent turns, the thread itself being shaped so as to have a substantially flat upper surface facing away from the first end of the implant so as to aid in the achievement of an intended, effective holding action such that the stress and strains set by chewing are distributed so as to minimize patient discomfort.

Another of these features pertains to the use of "cutting" notches at the first end of the member adjacent to the start of the thread so as to facilitate the insertion of the first end into the medullary region of a jaw bone as the implant is threaded in place.

Such insertion is facilitated in accordance with another aspect or feature of the invention by forming the second end so that it is perpendicular to the length of the implant and relatively flat so that if desired it can be driven in place, and by forming this second end so that it includes a centrally located, generally socket shaped hole leading from it toward the first end of the implant. The use of a socket permits the use of a non round tool such as an Allen wrench in installing the implant.

However, in accordance with this invention the socket is preferably not a conventional socket, but instead is internally threaded so that a post used in mounting a crown prosthesis can be threaded within it, or so tha such a post can be cemented in place within the socket in such a manner that a mechanical interlock is achieved between the post and the interior of the socket. As a consequence of this variety of ways that a crown prosthesis can be mounted it is possible to use a type of mounting as may be desired as a result of considerations which are not related to the invention.

Such features also include the use of a gradually tapered exterior on the member adjacent to the second end. This is preferred since it enables there to be a good deal of contact between the implant and a correspondingly shaped hole or opening in the cortical plate through which the implant extends when installed. This is considered desirable in minimizing the chances of soft tissue invasion with the jaw bone as the implant is used.

The last of these features pertains to the nature of the exterior of other than the second end of the implant. Preferably this exterior is, of course, formed of a biocompitable material which has been etched so as to have an actual surface area at least twice the actual or apparent surface area of the exterior. The latter may be expressed using terminology from the field of electrolytic capacitors by stating that the etch ratio of the exterior of the implant is at least two.

BRIEF DESCRIPTION OF THE DRAWING

Because of the nature of the invention it is best more fully described by referring to the accompanying drawing in which:

FIG. 1 is a cross sectional view showing a presently preferred dental implant of this invention installed in a jawbone;

FIG. 2 is a view corresponding to FIG. 1 showing the same implant with a post for mounting a crown prosthesis in place upon it;

FIG. 3 is a side elevational view, partially in section, at an enlarged scale of the implant shown in the preceding figures;

FIG. 4 is a plan view of the top or second end of the implant shown in FIG. 3;

FIG. 5 is a plan view of the bottom or first end of the implant shown in FIG. 3; and FIG. 6 is a side elevational view of the post shown in FIG. 2 at an enlarged scale.

It is to be understood that the invention is not be be considered as being limited by the accompanying drawing. This is because the drawing is intended solely for explanatory purposes. It is not intended to illustrate all aspects of the invention or all ways in which the features of it can be used. The implant illustrated incorporates the principles or concepts of the invention defined in the accompanying claims. Those skilled in the dental implant field can easily use these concepts or principles in somewhat differently appearing implants through the use or exercise of routine engineering skill in the implant field.

DETAILED DESCRIPTION OF THE PREFERRED EMBODIMENT

In the drawing there is shown a dental implant 10 in accordance with this invention which is preferably formed as a unitary member out of a biocompatible or reasonably biocompatible material such as titanium or the like so as to have a biocompatible exterior surface 12 which can be used in contact with medullary material 14 and the cortical or outer bone portion 16 of a complete bone 18 of an jaw (not shown) without danger of the implant 10 being rejected by the body. In theory, such a surface 12 can be a separate coating (not shown) provided on an implant which is of a different material than the material at or in the surface 12.

It is considered that preferred results are achieved when this surface 12 has been etched so as to increase its effective or actual surface area to as great an extent as reasonably possible. Such etching will, of course normally remove any surface contaminants or impurities on the surface 12 which might subsequently cause difficulty. However, it is not primarily used for this reason. When the surface has been etched to any significant extent it will contain surface irregularities which increase its actual surface area beyond what it originally was. As a consequence of this, an etched surface 12 is more receptive to growth when the implant 10 is used and as a result of this it can be considered that the increased surface area of the etched surface will promote adhesion or holding of the implant in place.

The etching techniques which can be used in etching the surface 12 can correspond to those used in etching the electrodes of electrolytic capacitors. For this reason they are not set forth in detail in this specification. Normally concentrated mineral acids are employed to etch such electrodes. It is considered that for any benefits of the etching to be apparent the surface 12 should be etched to at least such an extent that the etch ratio of surface areas is at least 2. In other words, the actual etched surface area should be at least twice that of the original or visually apparent surface area.

The implant 10 is shaped so as to include a nearly pointed first end 20 which is adapted to be inserted within the region 14 as the implant 10 is used. This end 20 is preferably slightly rounded so as to minimize unnecessary or undesired piercing occurring as the implant 10 is handled and utilized. Preferably this end is provided with two "cutting" notches 22 of a type such as are used upon self tapping screws or the like. These notches 22 are considered desirable in aiding in the installation of the implant 10 when an alveolar cavity is not perfectly shaped so as to receive it and in preventing rotation of the implant 10 after bone growth has occurred.

A thread 24 is located around the shank 26 of the implant so as to extend generally away from the end 20 so that the implant can be screwed down in place much in the manner in which a common wood screw is located in an operative position. Preferably the thread 24 used is shaped as shown so as to include a substantially flat upper or trailing surface 28 facing away from the end 20 and a tapered lower or leading surface 30 facing the end 20.

The shape of the upper surface 28 is considered important in obtaining an adequate holding action securing the implant 10 in place when it is used. The shape of the lower surface 30 is important in that it tends to distribute stresses which arise during chewing so that they generally extend outwardly from the shank 26 generally in the direction of the end 20. This is considered to minimize the chances of extreme stress causing physiological damage.

It is to be noted that the thread 24 is pitched as shown so that the thread 24 is spaced as illustrated in such a manner that the shank 26 is clearly visible. This is to provide spacing along the shank 26 such that growth can occupy the space around the shank 26 generally between the turns (not separately numbered) of the thread 24. This is considered important in achieving a good integration between the implant 10 and its bony substrate securing an implant 10 in place as it is used. Generally speaking, it is considered that the length of the space between the turns of the thread 24 should be at least 50% of the distance across the thread 24 in order to achieve an effective area for growth which will tend to hold the implant in place and that preferably this length should be at least as great as this distance.

An externally tapered portion or head 32 is located on the shank 26 remote from the first end 20 immediately adjacent to the second end 34 of the implant 10. This tapered portion or head 32 is preferred so that there will be a comparatively large area (not separately numbered) of contact between the head 32 and a correspondingly shaped opening 36 in the portion 16 of the bone 18 so as provide a sealing type area to minimize the chances of soft tissue invasion of the bone 18 as the implant 10 is used.

The second end 34 is preferably shaped as indicated so as to be substantially flat and perpendicular to the length of the shank 26 (and the implant 10) so that if desired it can be driven in place. However, normally it will be located by inserting an appropriate wrench (not shown) into a non-round socket 38 in this second end 34 and turning so as to "screw" the implant 10 in place. Preferably a hexagonal socket 38 is used since such a socket can be internally threaded as shown so as to contain internal threads 40 such that a threaded post stud 42 of a post 44 which is adapted to be used in mounting a crown prosthesis (not shown) can be screwed down into it.

With this construction, in effect the socket 38 is formed entirely within the threads 40 out of the threads. This type of construction is also desirable since it permits a non-threaded post (not shown) to be mounted within the socket 38 through the use of a conventional cement. Because of the presence of the threads 40 an effective holding action is achieved with any cement used in this manner.

I claim:

1. In an elongated member serving as a dental implant, said member having a first end which is adapted to be located within the interior of the alveolar cavity and a second end which is adapted to be secured to a prosthetic crown, said member having a biocompatible exterior, the improvement which comprises:

said second end of said implant includes an internally threaded cavity formed therein and a non-round socket formed as a part of said cavity, said cavity being useful both in installing said implant and in securing a post for mounting a prosthetic crown on said implant, a screw thread for use in mounting said first end within the interior of the alveolar cavity, said screw thread extending around and leading away from the first end of said member, the turns of said thread being spaced from one another so as to permit bond growth generally between adjacent turns of said thread, and said thread being shaped so as to have a flat surface facing away from said first end of said member for use in holding said member in place as it it is used and a tapered surface facing generally toward said first end of said member for use in distributing stress when said member is used.

2. An implant as claimed in claim 1 wherein:
said implant includes a tapered head adjacent to said second end, said head being shaped so as to fit against a hole in the cortical plate so as to minimize the entrance of soft tissue into the medullary region of a jaw bone when said insert is used.

3. An implant as claimed in claim 1 wherein:
said exterior surface of said implant is an etched surface having an actual surface area which is greater than its apparent surface area as a result of the presence of surface irregularities said etched surface being receptive to growth when said implant is used.

4. An implant as claimed in claim 1 wherein:
the turns of said thread are spaced apart a distance corresponding to at least 50% of the distance across said thread.

5. An implant as claimed in claim 1 wherein:
said first end is shaped so as a rounded point and so as to include cutting notch means for cutting into bond as said implant is installed and for holding said implant against rotation after bone growth has occurred.

6. An implant as claimed in claim 1 wherein:
said implant includes a tapered head adjacent to said second end, said head being shaped so as to fit against a hole in the cortical plate so as to minimize the entrance of soft tissue into the medullary region of a jaw bone when said insert is used, said exterior surface of said implant is an etched surface having an actual surface area which is greater than it apparent surface area as a result of the presence of surface irregularities, said etched surface being receptive to growth when said implant is used.

7. An implant as claimed in claim 6 wherein:
the turns of said thread are spaced apart a distance corresponding to at least 50% of the distance across said thread.

8. An implant as claimed in claim 6 wherein:
said first end is shaped so as a rounded point and so as to include cutting notch means for cutting into bond as said implant is installed and for holding said implant against rotation after bone growth has occurred.

9. An implant as claimed in claim 7 wherein:
said first end is shaped so as a rounded point and so as to include cutting notch means for cutting into bond as said implant is installed and for holding said implant against rotation after bone growth has occurred.

10. An implant as claimed in claim 1 wherein:
said implant includes a tapered head adjacent to said second end, said head being shaped so as to fit against a hole in the cortical plate so as to minimize the entrance of soft tissue into the medullary region of a jaw bone when said insert is used,
the turns of said thread are spaced apart a distance corresponding to at least 50% of the distance across said thread.

11. An implant as claimed in claim 10 wherein:
said first end is shaped so as a rounded point and so as to include cutting notch means for cutting into bond as said implant is installed and for holding said implant against rotation after bone growth has occurred.

12. An implant as claimed in claim 1 wherein:
said exterior surface of said implant is an etched surface having an actual surface area which is greater than it apparent surface area as a result of the presence of surface irregularities, said etched surface being receptive to growth when said implant is used,
the turns of said thread are spaced apart a distance corresponding to at least 50% of the distance across said thread.

13. An implant as claimed in claim 12 wherein:
said first end is shaped so as a rounded point and so as to include cutting notch means for cutting into bond as said implant is installed and for holding said implant against rotation after bone growth has occurred.

14. An implant as claimed in claim 1 wherein:
the turns of said thread are spaced apart a distance corresponding to at least 50% of the distance across said thread, and
said first end is shaped so as a rounded point and so as to include cutting notch means for cutting into bond as said implant is installed and for holding said implant against rotation after bone growth has occurred.

* * * * *